United States Patent
Jasra et al.

(10) Patent No.: US 9,725,383 B2
(45) Date of Patent: Aug. 8, 2017

(54) OXYGENATES-FREE C8-C12 AROMATIC HYDROCARBON STREAM AND A PROCESS FOR PREPARING THE SAME

(71) Applicant: Reliance Industries Limited, Mumbai (IN)

(72) Inventors: Rakshvir Jasra, Vadodara (IN); Prakash Kumar, Vadodara (IN); Jagannath Das, Vadodara (IN); Jince Sebastian, Idukki (IN)

(73) Assignee: Reliance Industries Limited (IN)

( * ) Notice: Subject to any disclaimer, the term of this patent is extended or adjusted under 35 U.S.C. 154(b) by 128 days.

(21) Appl. No.: 14/389,908

(22) PCT Filed: Apr. 1, 2013

(86) PCT No.: PCT/IN2013/000215
§ 371 (c)(1),
(2) Date: Oct. 1, 2014

(87) PCT Pub. No.: WO2013/175490
PCT Pub. Date: Nov. 28, 2013

(65) Prior Publication Data
US 2015/0073197 A1    Mar. 12, 2015

(30) Foreign Application Priority Data

Apr. 3, 2012  (IN) .................... 1089/MUM/2012

(51) Int. Cl.
| | | |
|---|---|---|
| *H01L 21/3065* | (2006.01) | |
| *C07C 7/13* | (2006.01) | |
| *C07C 7/12* | (2006.01) | |
| *C10G 25/03* | (2006.01) | |
| *C10G 25/05* | (2006.01) | |

(52) U.S. Cl.
CPC .............. *C07C 7/13* (2013.01); *C07C 7/12* (2013.01); *C10G 25/03* (2013.01); *C10G 25/05* (2013.01); *C07C 2529/06* (2013.01); *C10G 2300/1096* (2013.01); *C10G 2300/207* (2013.01); *C10G 2400/30* (2013.01)

(58) Field of Classification Search
None
See application file for complete search history.

(56) References Cited

U.S. PATENT DOCUMENTS

| | | |
|---|---|---|
| 4,954,325 A | 9/1990 | Rubin et al. |
| 5,427,689 A | 6/1995 | Kallenbach et al. |
| 6,111,162 A | 8/2000 | Rossini et al. |
| 7,102,044 B1 | 9/2006 | Kulprathipanja et al. |
| 7,576,248 B2 | 8/2009 | Kulprathipanja et al. |
| 7,709,692 B2 | 5/2010 | Das et al. |
| 2004/0242404 A1 | 12/2004 | Hwang et al. |
| 2005/0137442 A1 | 6/2005 | Gajda et al. |
| 2011/0077447 A1* | 3/2011 | Groothuis .......... B01D 53/1425 585/823 |
| 2013/0225898 A1* | 8/2013 | Sundaram ............ B01D 53/047 585/802 |
| 2013/0324774 A1* | 12/2013 | Riley ........................ C07C 2/64 585/315 |
| 2015/0025284 A1* | 1/2015 | Lowe .................... C10G 25/00 585/324 |

FOREIGN PATENT DOCUMENTS

| | | |
|---|---|---|
| EP | 0632120 | 1/1995 |
| GB | 899314 | 6/1962 |
| WO | WO 00/35836 | 6/2000 |
| WO | WO 2011/112189 | 9/2011 |

OTHER PUBLICATIONS

International Search Report of the International Searching Authority mailed on Sep. 26, 2013, issued in connection with International Application No. PCT/IN2013/000215 (4 pages).

Indian Patent Application No. 3205/MUM/2010, filed on Nov. 23, 2010 entitled "A Method for the Preparation of MWW Type Zeolite," filed in the name of Reliance Industries Limited (35 pages).

* cited by examiner

*Primary Examiner* — Tam M Nguyen
(74) *Attorney, Agent, or Firm* — McCarter & English, LLP

(57) ABSTRACT

The present disclosure provides a process for separating oxygenates present in an aromatic hydrocarbon stream to obtain an oxygenates-free aromatic hydrocarbon stream. The process involves selectively removing oxygenates from the aromatic hydrocarbon stream by passing said stream through at least one zeolite based adsorbing material.

9 Claims, 3 Drawing Sheets

OXYGENATES-FREE C8-C12 AROMATIC HYDROCARBON STREAM AND A PROCESS FOR PREPARING THE SAME

RELATED APPLICATIONS

This application is a U.S. National Phase Application under 35 U.S.C. 371 of International Application No. PCT/IN2013/000215 filed Apr. 1, 2013, which claims the benefit of Indian Patent Application No. 1089/MUM/2012 filed on Apr. 3, 2012. The disclosures of these applications are incorporated herein by reference in their entireties.

FIELD OF THE DISCLOSURE

The present disclosure relates to a C8-C12 aromatic hydrocarbon stream which is free from oxygenate contaminants and a process for preparing the same.

BACKGROUND

Catalytic reforming process in oil refinery processes leads to byproducts of hydrocarbon mixtures containing C8+ aromatics fractions. Such streams are generally fractionated to C8 aromatic cut, C9 aromatics cut and so on. Each of the fractions are processed to recover value added products, for example C8 cut is processed for recovery of para-xylene, C9-C12 cut finds application for either separation of specific valuable component like naphthalene, or fractioned for use as solvent, or blending stock in gasoline or diesel or fuel oil etc. The presence of oxygenates in the C8-C12 stream usually reduces the calorific value of the stream for uses such as fuel for combustion. The reduction in calorific value from the hydrocarbon to its corresponding oxygenates, (c.a. toluene to benzaldehyde, ethylbenzene to acetophenone etc.,) as disclosed by Dimitri Konovalov, in the article titled "The Calorific Value of Carbon Compounds", JCS rans. 1923, 123, 2184-2202, is provided herein below.

| Hydrocarbon | Q (Kcal/Mol) | Corresponding oxygenate | Q (Kcal/Mol) |
|---|---|---|---|
| Toluene | 934.4 | Benzaldehyde | 842.1 |
| Xylene | 1092 | Acetophenone | 1001.9 |

In any of these applications, it is always important to avoid formation of oxygenated compounds through auto-oxidation. The side-chains in these C8-C12 aromatics are always susceptible for auto-oxidation on exposure to air or oxygen and the propensity of auto-oxidation enhances with increase in number of carbon atoms in the side-chain. Thus it becomes an unavoidable necessity to preserve all these streams with elaborate arrangement of nitrogen blanketing in order to prevent exposure to air or oxygen. Therefore, it would be of significant industrial importance to develop an adsorptive method to remove or reduce the trace concentration of auto-oxidation products from these streams by using the suitable novel adsorbent compositions and adsorption processes.

To illustrate, further, the C8 cut, obtained in the refining or petrochemical processes, as described earlier, is meant for recovery of para-xylene and should be free from any oxygenated compound like aceto-phenone. Another illustration could be the C10 aromatic stream containing diethyl benzenes. A mixture of diethyl benzenes (obtained as by-product in styrene manufacture from ethyl benzene), are sometimes employed for recovery of para-diethyl benzene using a high pressure simulated moving bed adsorptive process using specific adsorbent, (a process developed by M/s Universal oil Products, USA), wherein it is of utmost importance that the feed stock diethyl benzene mixture should be essentially free from oxygenates or the auto-oxidation products of diethyl benzene, namely 4-ethyl benzaldehde, 4-ethyl acetophenone, 1,4 benzaldehyde, 4-acetyl acetophenone etc. It also equally holds good for the para-diethyl benzene product, a de-sorbent material, which finds use for separation of paraxylene through the well known "PAREX" process, wherein the stringent specification of the auto-oxidation products are very important. Normally the de-sorbent (para-di-ethyl benzene should essentially be free from auto-oxidation products, typically less than 1 ppm). It is to be born in mind that the same specification would be applied to the para-di-ethyl benzene (the desorbent in "PAREX" process), irrespective of the process or method of manufacturing the de-sorbent, either through disproportionation of ethyl benzene, or ethylation of ethyl benzene. Alternatively, the para-diethyl benzene could also be produced from non-conventional aromatics stream such as Mixed Xylene Solvent, containing predominantly a mixture of ethyl benzene and xylenes as described in the U.S. Pat. No. 7,709,692. However, as mentioned earlier, in any case, the desorbent (para-diehtyl benzene) should be essentially free from auto-oxidation product and the other oxygenates.

There have been several different adsorption schemes proposed for removal of oxygenated hydrocarbons but mostly are paraffinic in nature. For example, U.S. Pat. No. 6,111,162 discloses that hydrocarbons with 3 to 8 carbon atoms are treated for removal of oxygenated contaminants by an adsorbent comprising silica gel.

U.S. Pat. Nos. 7,576,248 and 7,102,044 discloses a process for removal of one or more oxygenates from C10-C15 olefin rich paraffin streams by passing the stream through an adsorbent bed comprising activated alumina, silica gel and sodium X zeolites.

U.S. Pat. No. 5,427,689 discloses how a variety of polar substances, including water, alcohols, ethers, aldehydes, ketones, amines, mercaptans, organic sulfides and carboxylic acids are removed from a hydrocarbon containing 1 to 10 carbon atoms using an absorbent composition comprising aluminum borate and zirconium borate.

Though, various processes, mainly involving the use of adsorbents for the removal of the oxygenates from the paraffinic hydrocarbon streams have been widely reported, processes for removal of the carbonyls from C8-C12 aromatic streams in general and from C10 aromatics in particular, and more specifically from para-diethyl benzene, by using adsorbents have not been reported.

The existing methods for the removal of carbonyl from aromatic streams of the kind mentioned above comprises of classical chemical method of treatment with reducing agent such as lithium aluminium hydride or sodium borohydride. Such methods consists of firstly treating the said stream with said reducing agent in the presence of methanol, followed by decomposing the extra amount of the reducing agent by addition of water and finally washing the stream to remove any excess alkali or reducing agent. Alternatively, the carbonyls could be destroyed by reducing with a metal and acid e.g. zinc and hydrochloric acid, followed by washing to remove acid/byproducts etc. Clearly, in such methods not only a large amount classical chemicals are used, but also a huge quantity of waste water is generated which is required to be further treated in an effluent treatment unit before disposal.

Another approach to remove particularly carbonyls from the said stream is solvent extraction using polar solvents such as methanol, ethanol, propanol, butanol etc, wherein the carbonyls are dissolved in the polar solvent and thereafter the solvents are separated by any known means such as settling and separation of layers, distillation etc.

Such methods have disadvantages such as the use of massive amount of solvents which is required to be purified before recycling through distillation, which in turn becomes both expensive (in terms of fixed and operating costs) as well as energy intensive.

In view of the above, there is therefore a need for a process for removal carbonyls from the aromatic hydrocarbon stream that overcomes the disadvantages associated with the classical chemical methods of the prior art.

DEFINITION

As used in the present disclosure, the following word/s and phrase/s are generally intended to have the meaning as set forth below, except to the extent that the context in which they are used to indicate otherwise.

The expression "Zeolite X" for the purpose of the present disclosure is composed of silica and alumina tetrahedral, joined together to form truncated octahedral or sodalite structure wherein the ratio of Si to Al is 1.25.

Objects:

Some of the objects of the present disclosure which at least one embodiment herein satisfies are as follows:

It is an objective of the present disclosure to provide a C8-C12 aromatic hydrocarbon stream which is free from oxygenate contaminants.

It is another object of the present disclosure to provide a process for preparing C8-C12 aromatic hydrocarbon stream which is free from oxygenate contaminants.

It is still another objective of the present disclosure to provide a process for simultaneous removal of the oxygenate contaminants and moisture form C8-C12 aromatic stream.

It is yet another objective of the present disclosure to provide a method for regeneration of the spent adsorbent by contacting the same with an aromatic stream.

Other objects and advantages of the present disclosure will be more apparent from the following description when read in conjunction with the accompanying figures, which are not intended to limit the scope of the present disclosure.

SUMMARY

In one aspect of the present disclosure there is provided a process for reduction of oxygenate from C8 to C-12 aromatic hydrocarbon stream comprising the following:
Passing the stream through a zeolite based adsorbing material at a Liquid Hourly Space Velocity (LHSV) ranging from 0.3 per hour to 4 per hour and recovering the stream with reduced oxygenate content.

Typically, the incoming stream has an oxygenate content ranging between 40 and 70 ppm and the stream with reduced oxygenate content has a content ranging between 0.5 and 3 ppm. Typically, the process of the present disclosure comprises the further step of regenerating the zeolite based adsorbing material after it is spent as a result of adsorbing oxygenates from the aromatic hydrocarbon stream.

Typically, the zeolite based adsorbing material is Zeolite X.

Typically, oxygenates include organic and inorganic oxygenates.

Typically, the oxygenate is water.

Typically, at least one oxygenate is an oxygenate selected from the group consisting of ketone, aldehyde and mixtures thereof.

Typically, the process of the present disclosure comprises the following further step:
Passing a slip stream containing reduced oxygenate content through the spent zeolite based adsorbing material at liquid hourly space velocity of 0.5 to 1.

Typically, the process of the present disclosure comprises the further step of feeding stream collected after regeneration of the adsorbing zeolite based material to the main stream for reduction of content of oxygenates.

Typically, the process of the present disclosure comprises the following step:
Passing the stream through a first column containing adsorbing zeolite based material at liquid hourly space velocity from 0.5 to 4 to provide stream with reduced oxygenate content, passing pre-determined portion of the recovered stream to a second column containing the spent adsorbing material to regenerate the spent adsorbing material and recovering the stream after it has regenerated the spent adsorbing material and recycling the recovered stream through the first column.

Typically, the aromatic hydrocarbon stream is passed alternately through the first and the second column.

BRIEF DESCRIPTION OF THE ACCOMPANYING DRAWINGS

DETAILED DESCRIPTION

Figure 1:
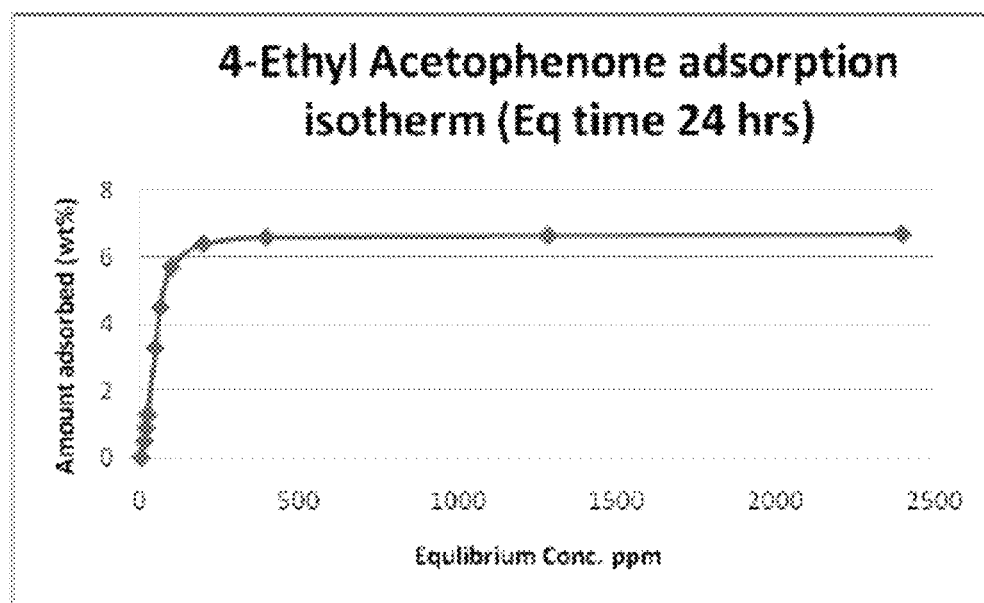
FIG. 1 illustrates equilibrium adsorption isotherm on Zeolite Na X with different 4-ethyl acetophenone concentration at 30° C.

The presence of undesired organic or inorganic oxygenated compounds in various mixtures or streams particularly the ones predominantly comprising aromatic hydrocarbons (C8-C12), always cause difficulty in processing these streams to obtain the desired value addition. For example recovery of para-xylene from the C8 aromatics streams is affected because of such contaminants present in the streams. Similarly the desorbents used for recovery of para-xylene in the well known PAREX process are required to be free from oxygenated compounds.

Typically, if the oxygenates are present in p-diethyl benzene it leads to poisoning of PAREX adsorbent. PAREX adsorbent is a very special and costly molecular sieve based adsorbent and is used for separation of para-xylene from a C8 aromatics stream containing ethyl benzene, meta-xylene, para-xylene and ortho xylene. Para-diethyl benzene is used as a solvent to desorb (called as desorbent), para-xylene in UOP's PAREX process. Poisoned PAREX adsorbent leads to reduction of para-xylene recovery which is undesirable. Hence it is desired to remove carbonyls/oxygenates from PDEB. Furthermore, the presence of such oxygenates (either the organic ones produced through auto-oxidation or the inorganic one e.g. dissolved water in the stream) can cause corrosion and erosion of the equipments when used at substantially severe conditions of temperature and pressure.

The term organic oxygenated compounds used herein is to mean essentially products of auto-oxidation of the aromatic compounds present in the mixtures/streams containing C8-C12 aromatic hydrocarbons under ambient conditions, i.e., mainly the aldehydes and ketones and the possible isomers thereof, but not limited to these only. The inorganic oxygenated compound is meant for water or dissolved moisture in the aromatics stream.

Thus, the present disclosure is directed to separate oxygenates from the mixtures/streams comprising aromatic hydrocarbons by contacting such mixtures/streams with a zeolite based adsorbent under conditions sufficient to provide products essentially free from the said oxygenated contaminants. The present disclosure also encompasses a method for regeneration of the spent or used adsorbent, (i.e., after the capacity of the adsorbent is exhausted for removal of the contaminants from the contaminated mixture comprising C8-C12 aromatic hydrocarbon/stream), by contacting the spent adsorbent with the stream containing reduced oxygenate content under conditions sufficient to provide a regenerated adsorbent having capacity similar or equivalent to the fresh adsorbent.

In accordance with first aspect of the present disclosure there is provided a process for separating oxygenates present in C8-C12 aromatic hydrocarbon stream.

The present process involves the following steps:

In the first step, oxygenates present in an aromatic hydrocarbon stream are selectively adsorbed by passing the aromatic hydrocarbon stream through a zeolite based adsorbent.

The aromatic hydrocarbon is at least one aromatic hydrocarbon selected from the group consisting of C8-C12 aromatic hydrocarbons.

Typically, the C8 aromatic hydrocarbon comprises at least one C8 aromatic hydrocarbon selected from the group consisting of ethyl benzene and xylenes.

In accordance with one of the preferred embodiments of the present disclosure the C8 aromatic hydrocarbon comprises ethyl benzene and xylenes wherein the content of ethyl benzene is in the range of 10 to 90%.

Typically, the C9 aromatic hydrocarbon comprises at least one C9 aromatic hydrocarbon selected from the group consisting of trimethyl benzenes, ethyl toluenes, isopropyl benzene and n-propyl benzene.

Typically, the C10 aromatic hydrocarbon comprises at least one diethyl benzene.

Typically, diethyl benzene is selected from the group consisting of meta-diethyl benzene, para-diethyl benzene and ortho-diethyl benzene. Alternatively, the C10 aromatic hydrocarbon comprises at least one compound selected from the group consisting of butyl benzenes, tetramethyl benzenes, methyl propyl benzene and dimethyl ethylbenzenes.

The C11 aromatic hydrocarbon comprises at least one compound selected from the group consisting of pentyl benzenes, penta-methyl benzenes, methyl diethyl benzenes, methyl butyl benzenes, dimethyl propyl benzenes, ethyl propyl benzenes and trimethyl ethyl benzenes.

Typically, the C12 aromatic hydrocarbon comprises at least one compound selected from the group consisting of hexyl benzene, hexa-methyl benzene, dimethyl diethyl benzene, dimethyl butyl benzene, ethyl butyl benzene, trimethyl propyl benzene and di-propyl benzene.

In the present context oxygenates or contaminants include inorganic oxygenates and organic oxygenates.

The organic oxygenates are resultant auto-oxidation products of the components present in said aromatics stream. Said organic oxygenates are corresponding carbonyl compounds. Particularly, the organic oxygenates are corresponding aldehyde or ketone compounds of the components present in the said aromatic stream. In accordance with the preferred embodiment of the present disclosure the organic oxygenated contaminants are selected from the group consisting of methyl benzaldehyde, ethyl benzaldehyde, ethyl acetophenone, ethyl propiophenone, propyl acetophenone, butyl acetophenone, pentyl acetophenone, phenyl acetaldehyde, benzophenone, n-butyrophenone, benzyl phenyl ketone, and isomers or mixtures thereof.

Typically, the inorganic oxygenate is at least one compound selected from the group consisting of compounds of hydrogen and oxygen but not having carbon, preferably the inorganic oxygenate is water.

In the final step, the stream with reduced oxygenate content is recovered.

In accordance with one of the embodiments of the present disclosure the adsorbing material used is zeolite based adsorbing material having MWW structure which includes MCM-22 and ITQ-2.

The method step of passing aromatic hydrocarbon stream is carried out using at least one technique selected from the group consisting of fixed bed, fluidized bed, moving bed, simulated moving bed, liquid phase and vapour phase. Typically, the flow of fluid is in a direction selected from the group consisting of upward and downward.

In accordance with one of the embodiments of the present disclosure the method step of passing is carried in a fixed bed system with either up-flow or down-flow. The choice of passing aromatic hydrocarbon stream through zeolite based adsorbent may vary depending on the type of the mixture/stream considered and the adsorbent chosen for the purpose. The method step of passing is carried out at a temperature above the freezing point of the mixture/stream in consideration to a temperature above the boiling point of the mixture/stream.

For a liquid phase operation, the range of temperature may be in the range from above the freezing point of the mixture/stream to a temperature below the boiling point of the stream. For example for a mixture containing a C8 aromatic stream it may be in the range of from −50 to 130° C., preferably from 0 to about 150° C., while for a mixture comprising C10 aromatics stream containing diethyl benzenes, it may be in the range of −50° C. to about 180° C. However in certain cases, it may also be carried out at a temperature in the range of about 10 to 100° C.

The pressure during the method step of passing the aromatic stream through zeolite based adsorbent also depends on the choices of the mixture/stream and the adsorbent. In general, the operating pressure may vary from sub-atmospheric to super atmospheric or the super critical pressure of the mixture/stream at the temperature of operation in the particular case of mixture/stream and the adsorbent. For liquid phase operation of the treatment method, it might be necessary to have adequate pressure to maintain the liquid phase of the mixture/stream at the temperature of operation. Thus it may be operated from ambient to 100 bar pressure.

The amount of mixture/stream passed over the unit mass of the adsorbent, defined as liquid hourly space velocity, may be in the range of from 0.1 per hr to 20 per hour. The choice of liquid hourly space velocity would be dependent on not only the selection of the mixture/stream and the adsorbent used for the purpose of treating, but also on the choice of the operating conditions and the desired output in terms of extent of removal of the contaminants sought for. For a target output auto-oxidation product in the treated mixture/stream for example, less than one ppm, it has been found to conduct the treatment method at a liquid hourly space velocity in the range from 0.1 to 50 per hour, preferably in the range from 0.1 to 20, more preferably from 0.3 to 4 per hour.

The process of the present disclosure further comprises passing an aromatic stream with reduced oxygenate contents through the spent zeolite based adsorbent at a liquid hourly space velocity of 0.5 to 1.

A wide variety of adsorbing materials that can be employed include silica (silica, silica gel, fumed silica), alumina (spherical or cylindrical extrudates of alumina), clay (montmorillonite, bentonites and kaolin) and molecular sieve and various commercial variants thereof.

The adsorbing material of particular interest in the context of the present disclosure however, is a zeolite based material. Many variants of zeolite are known however, the scope of the present disclosure is particularly restricted to naturally occurring or synthetic zeolite or molecular sieve having large or extra large pore apertures, preferably from the group of faujasite zeolite (zeolite X and zeolite Y), VPI-5, SSZ, zeolite beta, ZSM-12, including those of MWW structure such as MCM-22, ITQ-2, ITQ-5 and meso-porous molecular sieve materials like MCM-41 type.

The inventors of the present disclosure have found that the use of the zeolite based adsorbing material especially the ones with MWW structure (For Example, MCM-22, ITQ-2) results in reduction of the carbonyl number of the resulting aromatic stream, when expressed in terms of percentage reduction is in the range of about 92 to 100%. In accordance with a preferred embodiment of the present disclosure, the reduction in carbonyl number when expressed in terms of percentage is 100.

In accordance with another embodiment of the present disclosure the zeolite based adsorbing material is Zeolite X. Zeolite X is composed of silica and alumina tetrahedral joined together to form truncated octahedral or sodalite structure (Si/Al=1.25). These sodalite units are connected with tertiary units to form the structured zeolite unit cell. While $SiO_2$ groups are elctroneutral. $AlO_2$ groups are not and thus introduce an negative charge to the structure which is offset by the charge compensating, extra framework cations (eg, $Na^+$, $Li^+$, $Ca^{2+}$, $Ba^{2+}$). These extra framework cations are largely responsible for adsorption of oxygenates from feed mixture comprising of C8-C12 aromatic hydrocarbons.

The reduction in carbonyl number when expressed in terms of percentage is in the range of about 98 to 100%.

More detailed information on MWW type zeolite is provided in U.S. Pat. No. 4,954,325 (1990) and co-pending Indian Patent Application 3205/MUM/2010. More information on ITQ-2 zeolites is available in the paper published by A. Corma et. al. in Nature, (Lond.) 1998, 396, 353.

The selected zeolite or the molecular sieve may be used as such as available in the naturally occurring form or may be modified through ion-exchange. The adsorbent material of the present disclosure as described herein may be composited with a suitable inert binder and shaped suitably for commercial operation either in a fixed bed or moving bed or fluidized bed operation of the process. The binder may be selected from any of the inert binder materials well known in the art including clays, refractory metal oxides and alkali metal silicates which are used for shaping the zeolite or molecular sieve into various shapes. The shape of the adsorbent might be pellet, micro-sphere, sphere, cylindrical extrudates, trilobe, quadrulobe, or any other from as might be suitable for the purpose of smooth operation of the process. However, it has been found to be convenient to use either spherical bead or extrudate shape of the adsorbent when the process is operated in a fixed bed system.

In accordance with another embodiment of the present disclosure the process further involves a method step of regeneration of the spent or used adsorbent. The method step of regeneration of the spent adsorbent involves contacting the spent adsorbent with the contaminant-free aromatics stream under conditions sufficient to provide a regenerated adsorbent having capacity similar or equivalent to the fresh adsorbent. Inventors of the present disclosure during experimentation found that when the spent adsorbent is contacted with the stream containing reduced oxygenate (slip stream) at a liquid hourly space velocity of 0.5 to 1 then the capacity of the regenerated adsorbent is remarkably improved as compared to the spent adsorbent and is similar or equivalent to the fresh adsorbent.

In one embodiment of the present disclosure the process of the present disclosure comprises a step of passing the aromatic stream through a first column containing zeolite based adsorbent at a Liquid Hourly Space Velocity from 0.5 to 4.0 to obtain a stream with reduced oxygenate content. This stream with reduced oxygenate content in a predetermined quantity/portion is passed through a second column containing spent zeolite based adsorbent under conditions sufficient to obtain regenerated zeolite based adsorbent having capacity similar or equivalent of the fresh adsorbent. The regenerated zeolite based adsorbent is then recycled to the first column. The aromatic hydrocarbon stream with reduced oxygenate content is passed alternately through the first and the second column. The aromatic hydrocarbon stream collected after regeneration of the zeolite based adsorbent is recycled to the main stream for reduction of oxygenates content.

In accordance with an exemplary embodiment of the present disclosure the oxygenate content of the aromatic hydrocarbon stream before passing through the zeolite based adsorbent ranges between 40 and 70 ppm whereas the oxygenate content of the aromatic hydrocarbon stream after passing through the zeolite based adsorbent ranges between 0.5 and 3.0 ppm In accordance with another aspect of the present disclosure there is provided an oxygenates-free product comprising aromatic hydrocarbon/stream obtained by the process of the present disclosure.

In accordance with the present disclosure the aromatic hydrocarbon is selected from the group consisting of C8-C12 aromatic hydrocarbons and mixtures thereof.

The C8 aromatic hydrocarbon comprises at least one C8 aromatic hydrocarbon selected from the group consisting of ethyl benzene and xylenes.

In accordance with one of the preferred embodiments of the present disclosure the C8 aromatic hydrocarbon comprises ethyl benzene and xylenes wherein the content of ethyl benzene is in the range of 10 to 90%.

The C9 aromatic hydrocarbon in accordance with the present disclosure comprises at least one C9 aromatic hydrocarbon selected from the group consisting of trimethyl benzenes, ethyl toluenes, isopropyl benzene, and n-propyl benzene.

Typically, the C10 aromatic hydrocarbon comprises at least one diethyl benzene. Typically, diethyl benzene is selected from the group consisting of meta-diethyl benzene, para-diethyl benzene and ortho-diethyl benzene.

Alternatively, the C10 aromatic hydrocarbon comprises at least one compound selected from the group consisting of butyl benzenes, tetramethyl benzenes, methyl propyl benzene and dimethyl ethylbenzenes.

Typically, the C11 aromatic hydrocarbon comprises at least one compound selected from the group consisting of pentyl benzenes, penta-methyl benzenes, methyl diethyl benzenes, methyl butyl benzenes, dimethyl propyl benzenes, ethyl propyl benzenes and trimethyl ethyl benzenes.

The C12 aromatic hydrocarbon comprises at least one compound selected from the group consisting of hexyl benzene, hexa-methyl benzene, dimethyl diethyl benzene, dimethyl butyl benzene, ethyl butyl benzene, trimethyl propyl benzene and di-propyl benzene.

In accordance with the present disclosure oxygenates are selected from the group consisting of organic oxygenates and inorganic oxygenates. The organic oxygenates are auto-oxidation products of the components present in said stream. Said organic oxygenates are carbonyl compounds selected from the group consisting of methyl benzaldehyde, ethyl benzaldehyde, ethyl acetophenone, ethyl propiophenone, propyl acetophenone, butyl acetophenone, pentyl acetophenone, phenyl acetaldehyde, benzophenone, n-butyrophenone, benzyl phenyl ketone and mixture thereof.

The inorganic oxygenate is at least one compound selected from the group consisting of compounds of hydrogen and oxygen but not having carbon, preferably the inorganic oxygenate is water.

Analysis of the treated mixture/stream for the auto-oxidation products of the components present therein, is very important since it deals with the resultant values in the range of ppm level. A preferred method for the purpose is the one which is long established and is accepted one by the authority of American Standard Testing Method. Thus for the purpose of analysis of the auto-oxidation products of the components of C8-C12 aromatic mixture/stream (usually the aldehydes and ketones of the corresponding aromatic compound, generally referred as carbonyls), was carried out by following the method prescribed by ASTM-E 411-70.

The carbonyls (aldehyde and ketones) are measured by a chemical analysis method and are reported as "Carbonyl number". The Carbonyl number is defined as milligrams of carbonyl functional per liter of the sample using acetaphenone as a standard. Carbonyl number of PAREX desorbent (paradiethylbenzene) is determined by a chemical method which determines carbonyl number in the range of 0.1 to 100 mg/liter as ketone or aldehyde in hydrocarbons. The carbonyl compounds in the sample are extracted with acidic, alcoholic 2,4 dinitrophenyl hydrazine to form phenyl hydrazone. Alcoholic potassium hydroxide is added to stop the reaction and convert the yellow hydrazone to a pink compound. The color intensity of the pink compound is measured at 480 nm in UV visible spectrophotometer and the carbonyl content of the sample is determined from a standard calibration curve from which the carbonyl number is determined as per ASTM method E 411-70.

These results are normally used as indication of oxygen exposure of the PAREX and Molex feed stocks.

In addition, further analysis was carried out to complement the results from the ASTM E 411-70, by following a high performance gas chromatographic (GC) method, to capture any of the left out auto-oxidation product or other oxygenates. The GC analysis was carried out using a gas chromatograph equipped with a flame ionization detector and DB Wax column of 60 m length, 0.32 mm diameter and 0.50 μm film thickness. Helium was employed as carrier gas at a flow rate of 2.3 ml/min in constant flow mode. Inlet temperature was maintained at 230° C. and FID at 250° C. Oven temperature was programmed in the range of 50 to 220° C. as given below:

| # | Rate | Temp, ° C. | Time, min |
|---|------|------------|-----------|
| 1 |      | 50         | 5         |
| 2 | 8    | 100        | 0         |
| 3 | 2    | 120        | 0         |
| 4 | 10   | 220        | 15        |

Moisture analysis of the samples were carried by ASTM Method D 6304, "Determination of Water in Petroleum Products, Lubricating Oils, and Additives by Coulometric Karl Fischer Titration,"

It is to be understood that treatment of mixture/stream with zeolite is well known in art for moisture and olefinic impurities removal, however treatment of C8-C12 aromatic mixture/stream with simultaneous removal of oxygenated contaminants (resulting from auto-oxidation of the components or inadvertently contaminated otherwise) as well as inorganic ones, such as moisture, are hitherto not known in the prior art.

It has been found that the treated stream is much more convenient and suitable for further applications or processing. For example, the treated C8 aromatic stream, when free from such contaminants becomes useful for recovery of para-xylene; the C10 aromatic stream consisting of di-ethyl benzene becomes suitable for recovery of paradiethyl benzene; and even when a pure para-diethyl benzene gets contaminated with the auto-oxidation product, such treatment results in a product which is useful for application as a desorbent in PAREX process.

Experiments carried out for performance evaluation of the adsorbents covered determination of the adsorption capacity of the adsorbents both in equilibrium adsorption method as well as adsorption breakthrough mode, as described herein after in the examples (vide supra). Special care was taken during the experiments to avoid any exposure of the adsorbent and the aromatic stream to air/oxygen.

The present disclosure also encompasses a method for regeneration of the spent adsorbent, or the adsorbent after it had exhausted its capacity for adsorption of the contaminants. Procedures for regeneration of the adsorbent could be in-situ or ex-situ, or by calcinations of the adsorbent at a high temperature in the range of 200-600° C. in an oxidizing atmosphere, or desorption of the adsorbed contaminants by using the treated aromatic stream. The conditions for regeneration could vary in a wide range depending on the total amount contaminants already adsorbed on the adsorbent or it may be similar to those as it were in the case of treatment of the contaminated stream. However, the preferred range of conditions for regeneration of the adsorbent include a temperature from about 20° C. to about 300° C., a pressure from about 1 to about 20 atmospheres, and a liquid hourly space velocity from about 0.1 to about 20 $hr^{-1}$.

In order to illustrate the present disclosure and the advantages thereof, the following examples are provided. It is understood that these examples are illustrative and do not provide any limitation on the disclosure in the manner in which it can be practiced.

Example 1

1 g of zeolite NaX (1 to 1.5 mm beads) previously activated at 350° C. and cooled under nitrogen atmosphere was taken in a previously nitrogen flushed air tight vial to which 10 ml of C8 Aromatic hydrocarbons stream having composition as shown in table 1 and containing 100 ppm acetophenone impurity, was added. Vial containing the mixture was allowed to equilibrate for 12 hrs in a shaker at 25° C. and was analyzed using GC method. It was observed that acetophenone concentration got reduced from 100 ppm to 5 ppm after 12 hrs. The decrease in acetophenone impurity was 95%.

TABLE 1

Composition of C8 Aromatic Stream

| | |
|---|---|
| Non Aromatics | <0.01 wt % |
| Benzene | <0.01 wt % |
| Toluene | <0.01 wt % |
| Ethyl Benzene | 64.6 wt % |
| para-Xylene | 7.6 wt % |
| Meta-Xylene | 18.2 wt % |
| Ortho-Xylene | 9.3 wt % |
| C9 + C10 Aromatics | 0.3 wt % |

Example 2

1 g of zeolite NaX (1 to 1.5 mm beads) previously activated at 350° C. and cooled under nitrogen atmosphere was taken in a previously nitrogen flushed air tight vial to which 10 ml of C8-C10 aromatic hydrocarbon mixture (as shown in table 2) and having carbonyl number 6.5 was added. Vial containing the mixture was allowed to equilibrate for 12 hrs in a shaker at 25° C. and total carbonyls were measured by UV method (ASTM-E-411-70). It was noted that carbonyl number got reduced to 1.5 after 12 hrs. Thus the reduction in carbonyl number was about 77%.

TABLE 2

Composition of C8-C10 Aromatics Stream

| | |
|---|---|
| Benzene | <0.01 wt % |
| Toluene | <0.01 wt % |
| Ethyl Benzene | 56.2 wt % |
| para-Xylene | 7.8 wt % |
| Meta-Xylene | 18.2 wt % |
| Ortho-Xylene | 9.4 wt % |
| C9 Aromatics | 0.4 wt % |
| meta-Diethyl Benzene | 1.5 wt % |
| Para-Diethyl Benzne | 4.9 wt % |
| C10+ Aromatics | 1.6 wt % |

Example 3

1 g of zeolite NaX (1 to 1.5 mm beads) previously activated at 350° C. and cooled under nitrogen atmosphere was taken in a previously nitrogen flushed air tight vial to which 10 ml of para-diethyl benzene (PDEB) having the composition as shown in table 3, and having carbonyl number 20 (as measured by UV method, ASTM-E411-70), was added. Vial containing PDEB and zeolite was allowed to equilibrate for 12 hrs in a shaker at 25° C. and total carbonyls were measured by UV method. It was found that carbonyl number decreased to <0.5 after 12 hrs, thus showing a reduction in carbonyl number by more than 97.5%.

TABLE 3

Composition of para diethyl benzene stream

| | |
|---|---|
| Non Aromatics | <0.01 wt % |
| Benzene | <0.01 wt % |
| Toluene | <0.01 wt % |
| Total C8 Aromatics | <0.01 wt % |
| Total C9 Aromatics | 0.05 wt % |
| meta di-ethyl benzene | 0.32 wt % |
| para di-ethyl benzene | 99.31 wt % |
| ortho di-ethyl benzene | 0.06 wt % |
| Heavy Boilers | 0.26 wt % |

Example 4

The untreated PDEB and the purified PDEB (obtained after the treatment with zeolite NaX) as described in Example 3 were further analyzed for moisture by following the procedure as given in ASTM D 6304. Moisture contents were found to be 300 ppm in the untreated PDEB to 18 ppm in the treated PDEB, showing 94% reduction in moisture through treatment.

Example 5

1 g of zeolite CaX (1 to 1.5 mm beads) previously activated at 350° C. and cooled under nitrogen atmosphere was taken in a previously nitrogen flushed air tight vial to which 10 ml of PDEB having carbonyl number 20 was added.

Vial containing PDEB and zeolite was allowed to equilibrate for 12 hrs in a shaker at 25° C. and total carbonyls were measured by UV method. It was observed that carbonyl number got reduced to <0.7 after 12 hrs. The reduction in carbonyl number was more than 96.5%.

Example 6

1 g of zeolite NaX (1 to 1.5 mm beads) previously activated at 350° C. and cooled under nitrogen atmosphere was taken in a previously nitrogen flushed air tight vials to which 10 ml of PDEB having varying concentration of 20 to 3000 ppm wt of 4 ethyl-acetaphenone were added. Sample vials were allowed to equilibrate for 24 hrs in a shaker at 25° C. 4-ethyl-acetophenone concentration was measured through gas chromatography. The results are plotted in FIG. 1.

Example 7

1 g of zeolite BaX (1 to 1.5 mm beads) previously activated at 350° C. and cooled under nitrogen atmosphere was taken in a previously nitrogen flushed air tight vial to which 10 ml of PDEB having carbonyl number 20 was added. Vial containing PDEB and zeolite was allowed to equilibrate for 12 hrs in a shaker at 25° C. and total carbonyls were measured by UV method. It was noted that carbonyl number got reduced to <1.2 after 12 hrs. The reduction in carbonyl number was more than 94%.

Example 8

1 g of Silica gel (1 to 2 mm beads) previously activated at 150° C. and cooled under nitrogen atmosphere was taken in a previously nitrogen flushed air tight vial to which 10 ml of PDEB having carbonyl number 20 was added. Vial containing PDEB and silica gel was allowed to equilibrate for 12 hrs in a shaker at 25° C. and total carbonyls were measured by UV method. It was measured that carbonyl number got reduced to <0.8 after 12 hrs. The reduction in carbonyl number was more than 96%.

Example 9

1 g of activated alumina (1 to 2 mm beads) previously activated at 200° C. and cooled under nitrogen atmosphere was taken in a previously nitrogen flushed air tight vial to which 10 ml of PDEB having carbonyl number 20 was added. Vial containing PDEB and alumina was allowed to equilibrate for 12 hrs in a shaker at 25° C. and total carbonyls were measured by UV method. It was measured that carbonyl number got reduced to <1.6 after 12 hrs. The reduction in carbonyl number was more than 92%.

Example 10

1 g of calcium bentonite (0.6 to 1.2 mm granules) previously activated at 200° C. and cooled under nitrogen atmosphere was taken in a previously nitrogen flushed air tight vial to which 10 ml of PDEB having carbonyl number 20 was added. Vial containing PDEB and bentonite was allowed to equilibrate for 12 hrs in a shaker at 25° C. and total carbonyls were measured by UV method. It was measured that carbonyl number got reduced to <1.8 after 12 hrs. The reduction in carbonyl number was more than 91%.

Examples 11-14

Figure 6:
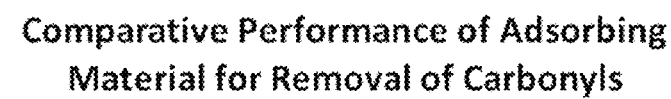
FIG. 6 illustrates comparative performance of adsorbing material for removal of carbonyls.

1 g of zeolite powder previously activated at 200° C. and cooled under nitrogen atmosphere was taken in a previously nitrogen flushed air tight vial to which 10 ml of PDEB stream (having composition essentially same as in table 3) but having carbonyl number 71 was added. Vial containing PDEB and zeolite adsorbent was allowed to equilibrate for 12 hrs in shaker at 25° C. and total carbonyls were measured by UV method. It was measured that carbonyl number got reduced to <1.8 after 12 hrs. Results on removal of carbonyl efficacy are given in table 4 and FIG. 6.

TABLE 4

Efficacy of different zeolites for removal of carbonyls from C10 aromatics stream.

| Example Nos | Adsorbent | Feed C10 Aromatics | Product C10 Aromatics | % removal of Carbonyls |
|---|---|---|---|---|
| Example 11 | MCM-22 (30*) | 71 | 0 | 100 |
| Example 12 | 13 X (Faujasite) | 71 | 0 | 100 |
| Example 13 | ITQ-2 (50*) | 71 | 5 | 93 |
| Example 14 | ITQ-2 (60*) | 71 | 6 | 92 |

*Values in parenthesis indicate silica to alumina ratio of corresponding zeolite Example 15

30 g of Zeolite NaX (1 to 1.5 mm granular sized) activated in furnace at 350° C. under nitrogen atmosphere was charged in a stainless steel tubular column of the dimension of 6 inch length X ½ inch internal diameter.

The adsorbent was further activated in column to remove any air and moisture ingress during loading of the adsorbent in flowing nitrogen heated from near ambient temperature to 220° C. at the heating rate of 2° C. per minute, and then it was held at 220° C. for another 2 hrs in continuous dry nitrogen flow. Finally the activated zeolite Na X adsorbent was cooled to ambient temperature under dry nitrogen flow.

After activation of the adsorbent, a PDEB feed containing 60 ppm w/w of 4-ethyl acetophenone (4-EAP) was fed in the column During the adsorption cycle, the PDEB feed rate was set at 0.7 cc/min to maintain a liquid hourly space velocity (LHSV) of 1 hr-1 (v/v/hr). The adsorbent bed was maintained at ambient temperature and pressure of 12 kg/cm2. Samples at the outlet of the column were collected in pre-nitrogen flushed close loop samplers.

Figure 2:
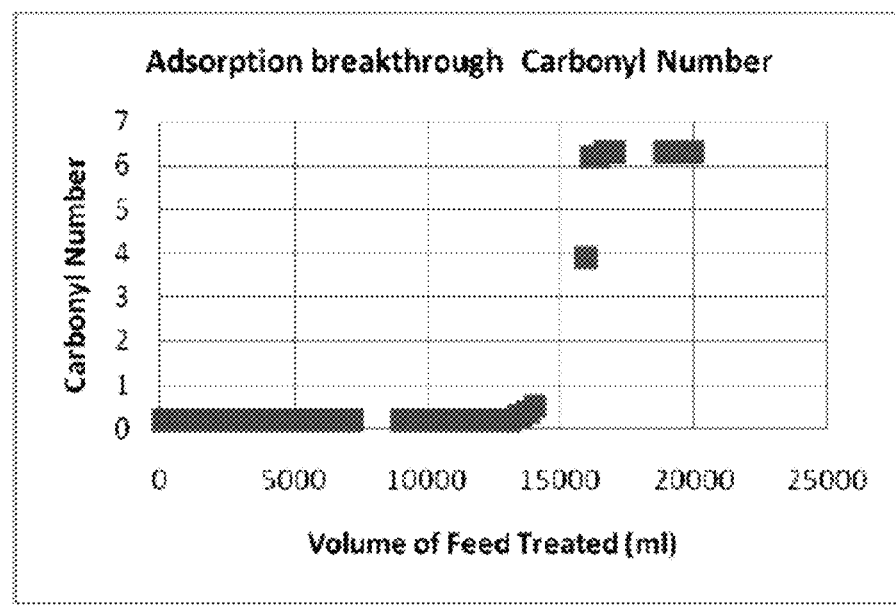
FIG. 2 illustrates adsorption breakthrough of total carbonyls on Zeolite Na X molecular sieve at 30° C.
Figure 3:
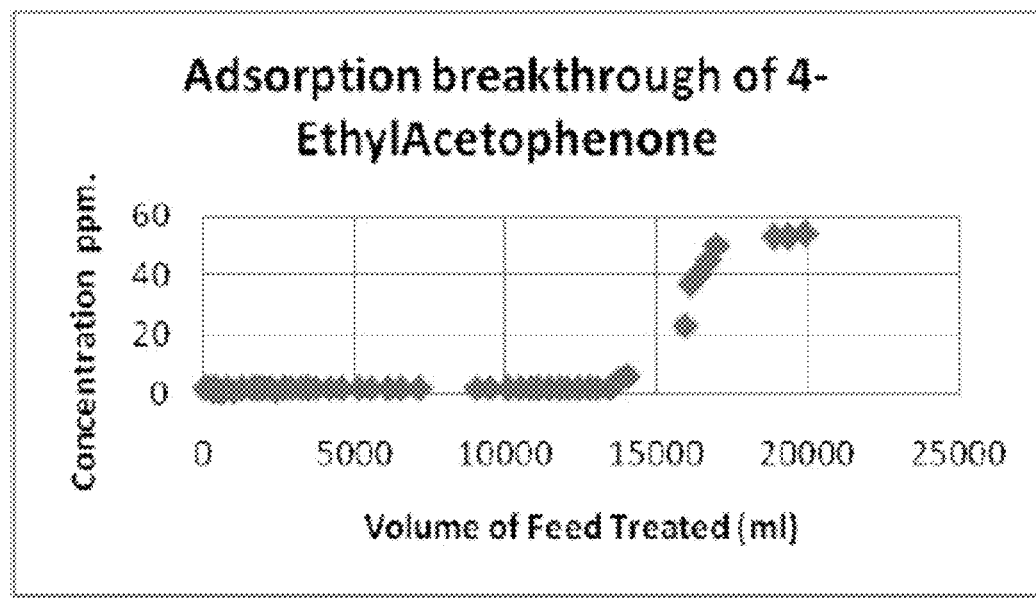
FIG. 3 illustrates adsorption breakthrough of 4-ethyl acetaphenone on Zeolite NaX molecular sieve at 30° C.

Total carbonyls in PDEB were estimated by UV method and the measured values are plotted as total carbonyls breakthrough (FIG. 2). The 4-ethyl acetophenone in the feed and treated samples was determined by GC analysis to ascertain the 4-ethyl acetophenone breakthrough curve as shown in FIG. 3.

The breakthrough point is defined as when 4-ethyl acetophenone concentration in the outlet product reached equal to or more than 2 ppm. The adsorbent could adsorb 3 wt % of the 4-EAP as estimated from adsorption breakthrough curve.

Example 16

Another adsorption breakthrough was conducted by following the procedure as described in example 11, wherein the adsorbent bed was maintained at a pressure 3 kg/cm2. The results were essentially same as those were obtained in case of example 11.

Example 17

After the completion of adsorption breakthrough adsorbent bed has reached its capacity, regeneration procedure was followed to remove the adsorbed carbonyl compounds from the adsorbent bed. Part of treated PDEB free of carbonyls passed passed through the bed in reverse direction at an elevated temperature for a sufficient period of time for the bed to be rejuvenated through the removal of the carbonyls. In one embodiment of the rejuvenation process bed temperature was elevated to 150° C. for 2 hrs, then to 220° C. for 4 hrs. Earlier treated PDEB free of carbonyls was passed through the bed at the LHSV of 1 until the adsorbent bed was completely regenerated. Regenerated bed was cooled to ambient temperature under treated PDEB flow. Post regeneration adsorbent bed adsorbed 2.5 wt % of the 4-ethylacetophenone as estimated from adsorption breakthrough curve.

Example 18

30 g of Zeolite NaX of the size of 1 to 1.5 mm granular sized activated in furnace at 350° C. under nitrogen atmosphere and was charged in a stainless steel tubular column of the dimension of 6 inch length X ½ inch internal diameter.

The adsorbent was further activated in column to remove any air and moisture ingress during loading of the adsorbent in flowing nitrogen heated from near ambient temperature to 220° C. at the heating rate of 2° C. per minute and the temperature was maintained at 220° C. for another 2 hours in continuous nitrogen flow. Finally the activated zeolite NaX adsorbent was cooled to ambient temperature under constant flow of dry nitrogen.

A PDEB feed containing 60 ppm w/w of 4-ethyl acetophenone (4-EAP) was fed in the column During the adsorption cycle, the PDEB feed rate was set at 2.0 cc/min to maintain a liquid hourly space velocity (LHSV) of 3 hr-1 (v/v/hr). The adsorbent bed was maintained at 50° C. and pressure of 2 kg/cm2. Samples at the outlet of the column were collected in pre-nitrogen flushed close loop samplers.

Figure 4:
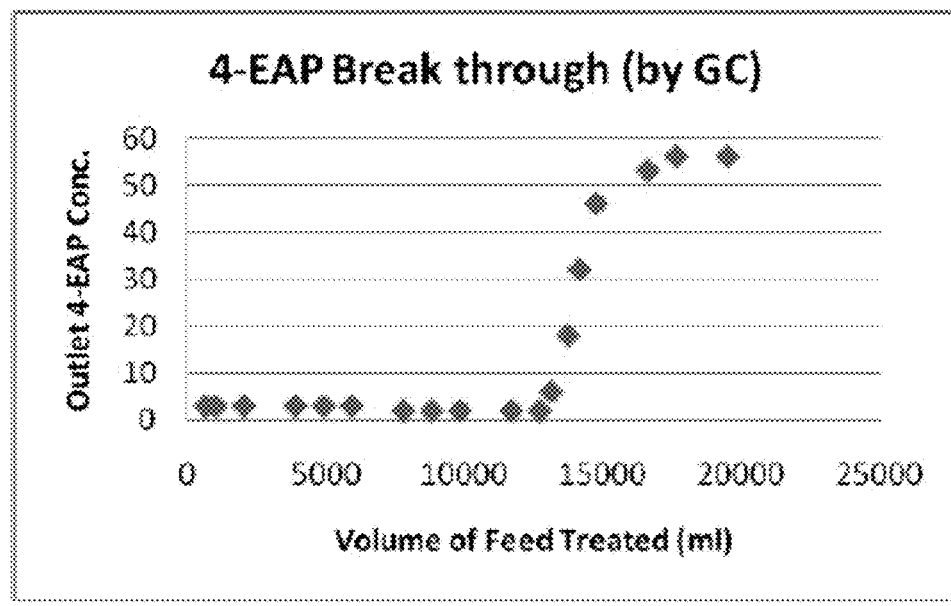
FIG. 4 illustrates adsorption breakthrough of total carbonyls on Zeolite NaX molecular sieve at 50° C.

The 4 ethyl acetophenone in the feed and treated samples was determined by GC analysis to ascertain the 4-ethyl acetophenone breakthrough curve as shown in FIG. 4. The breakthrough point was defined as when 4-ethyl acetophenone concentration reached equal to or more than 2 ppm in the outlet product.

Figure 5:
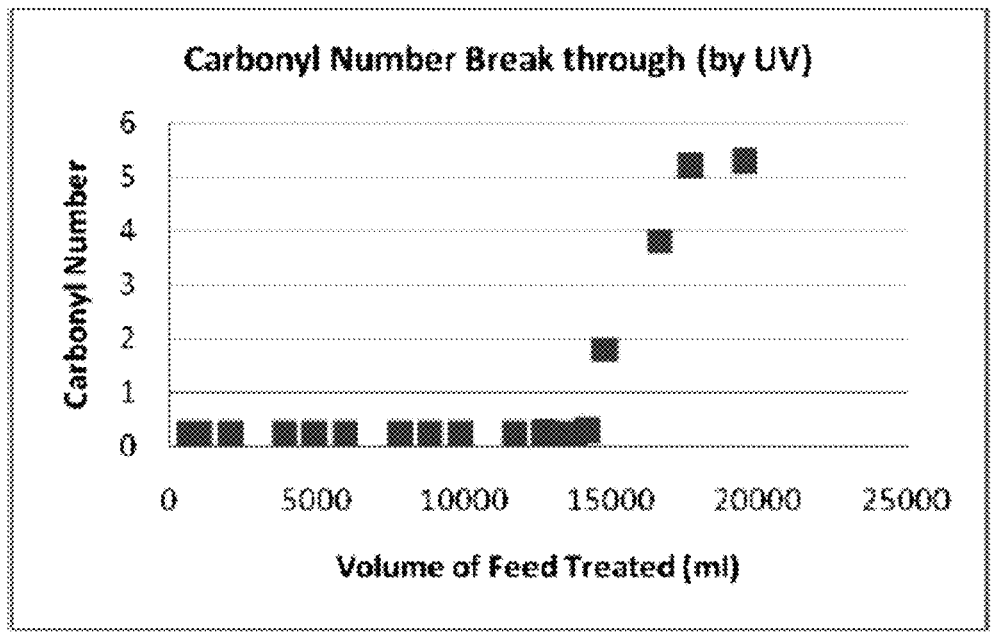
FIG. 5 illustrates adsorption breakthrough of 4-Ethyl acetaphenone on Zeolite NaX molecular sieve at 50° C.

Carbonyl Number was also estimated in PDEB by UV method and measured values are plotted in FIG. 5 as total carbonyls breakthrough.

Example 19

Part of treated para-diethyl benzene (PDEB) free of carbonyls from adsorbent bed ongoing under adsorption was passed in the form of slip stream through the previously carbonyls saturated zeolite X bed in reverse direction at an elevated temperature of 180° C. and 1.5 kg/cm2 pressure for 6 hrs at liquid hourly space velocity of 0.5 per hr to regenerate and bring down carbonyls number of 0.2. Regenerated bed was cooled to ambient temperature under slip stream carbonyl free PDEB flow. Post regeneration adsorbent bed adsorbed 2.5 wt % of the 4-ethylacetophenone as estimated from adsorption breakthrough curve compared to 2.7 wt % to the freshly charged bed.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary. Wherever a range of values is specified, a value up to 10% below and above the lowest and highest numerical value respectively, of the specified range, is included in the scope of the invention.

In view of the wide variety of embodiments to which the principles of the present invention can be applied, it should be understood that the illustrated embodiments are exemplary only. While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. A process for reduction of oxygenates present in $C_8$ to $C_{12}$ aromatic hydrocarbon stream, said process comprising the following steps:
    i. passing said $C_8$ to $C_{12}$ aromatic hydrocarbon stream, having oxygenates ranging between 40 and 70 ppm, through a zeolite based adsorbing material selected from the group consisting of Zeolite-X, Zeolite-Y, VPI-5, SSZ, Zeolite beta, ZSM-12, MCM-22, ITQ-2, ITQ-5, and MCM-41, at a Liquid Hourly Space Velocity (LHSV) ranging from 0.3 per hour to 4 per hour and recovering a stream with reduced oxygenates ranging between 0.5 and 3 ppm, wherein the zeolite based adsorbing material is used until it is spent as a result of adsorbing oxygenates from the aromatic hydrocarbon stream to obtain spent zeolite based adsorbing material; and
    ii. regenerating the spent zeolite based adsorbing material by passing a pre-determined portion of the recovered stream through the spent zeolite based adsorbing material to obtain a regenerated zeolite based adsorbing material.

2. The process as claimed in claim 1, wherein the oxygenates include organic and inorganic oxygenates.

3. The process as claimed in claim 2, wherein one of the inorganic oxygenates is water.

4. The process as claimed in claim 2, wherein the organic oxygenates are selected from the group consisting of ketone, aldehyde and mixtures thereof.

5. The process as claimed in claim 1, which comprises the following further step:
    passing a slip stream containing reduced oxygenates through the spent zeolite based adsorbing material at Liquid Hourly Space Velocity of 0.5 per hour to 1 per hour.

6. The process as claimed in claim 1, which includes the further step of feeding stream collected after regeneration of the adsorbing zeolite based material to the $C_8$ to $C_{12}$ aromatic hydrocarbon stream for reduction of oxygenates.

7. The process as claimed in claim 1, which comprises the following step:
    passing the $C_8$ to $C_{12}$ aromatic hydrocarbon stream through a first column containing the zeolite based adsorbing material at Liquid Hourly Space Velocity from 0.5 per hour to 4 per hour to obtain the recovered stream with reduced oxygenate content, passing a pre-determined portion of the recovered stream to a second column containing the spent zeolite based adsorbing material to regenerate the spent zeolite based adsorbing material and recovering the stream after it has regenerated the spent adsorbing material and recycling the recovered stream through the first column.

8. The process as claimed in claim 7, wherein the $C_8$ to $C_{12}$ aromatic hydrocarbon stream is passed alternately through the first and the second column.

9. The process as claimed in claim 1, wherein the pre-determined portion of the recovered stream is passed through the spent zeolite based adsorbing material at a temperature in the range of 20° C. to 300° C., at a pressure in the range of 1 atmospheres to 20 atmospheres, and at a Liquid Hourly Space Velocity in the range of 0.1 $h^{-1}$ to 20 $h^{-1}$.

* * * * *